(12) United States Patent
Falus et al.

(10) Patent No.: US 8,367,802 B2
(45) Date of Patent: *Feb. 5, 2013

(54) METHOD TO PRODUCE FIBRIN MONOMER IN ACID MEDIA FOR USE AS TISSUE SEALANT

(75) Inventors: George David Falus, New York City, NY (US); Leonid Medved, Ellicot City, MD (US)

(73) Assignee: Biomedica Management Corporation, Brooklyn, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/487,057

(22) Filed: Jun. 18, 2009

(65) Prior Publication Data

US 2010/0197893 A1    Aug. 5, 2010

(51) Int. Cl.
*A61K 38/36* (2006.01)
*A61K 38/00* (2006.01)

(52) U.S. Cl. .................. 530/344; 530/381; 530/382

(58) Field of Classification Search .................. None
See application file for complete search history.

(56) References Cited

U.S. PATENT DOCUMENTS 5,750,657 A * 5/1998 Edwardson et al. .......... 530/382

FOREIGN PATENT DOCUMENTS

EP    592242 A1 *  4/1994

OTHER PUBLICATIONS

Baldwin et al. (2010) Polysaccharide-Modified Synthetic Polymeric Biomaterials, Biopolymers, vol. 94, No. 1, pp. 128-140.*
Geer C.B. et al. (2007) A dissertation of Univ. North Carolina, "Analytical Studies on the Mechanism of Fibrin Formation", pp. 1-132.*

* cited by examiner

*Primary Examiner* — Manjunath Rao
*Assistant Examiner* — Samuel Liu (57) ABSTRACT

A hemostatic agent designed for use in cases of non-compressible hemorrhage. It can be applied through a mixing needle and/or a spray injection method following abdominal, chest, extremities or other intracavitary severe trauma to promote hemostasis, or it can be used for laparoscopic procedures or other surgical procedures in which compression is not possible or recommended. Its crosslinking technology generates an adhesive three-dimensional polymeric network or scaffold that carries a fibrin sealant required for hemostasis. When mixed, it produces a foam that spreads throughout a body cavity reaching the lacerated tissue to seal tissue and promote the coagulation cascade. The fibrin components are produced by a novel dialysis method which does not present thrombin to the immune system and can be maintained in solution for six weeks without significant proteolytic degradation.

10 Claims, 4 Drawing Sheets

| Fibrinogen | EDTA (4mM) | Clotability |
|---|---|---|
| | | 300 mM NaCl* |
| 5 mg/mL | + | 97% |
| 2 mg/mL) | + | 98% |
| 2 mg/ml | - | 94% |
| Medved's Method: Glass rod Spooling | - | 97% |

METHOD TO PRODUCE FIBRIN MONOMER IN ACID MEDIA FOR USE AS TISSUE SEALANT

FIELD OF THE INVENTION

The present invention is related to a method for the preparation of concentrated fibrin monomer in acid media for application as adhesive sealant component and hemostatic agent, which may be used to bond or seal tissue in vivo with or without compression. The preparation is particularly related to need of embedding a fibrin sealant in a scaffold which is applied to tissue and then cured in vivo in order to bond tissue, to seal tissue to prevent or control hemorrhage.

BACKGROUND OF THE INVENTION

There has been a renewed interest in the development of better hemostatic agents for traumatic injuries. (1, 2). As a result of their hemostatic and adhesive properties, sealants, and particularly fibrin sealants are extensively used today in most surgical specialties to reduce blood loss and post-operative bleeding because of the ability to adhere to human tissue as it polymerizes (3,4). These compounds are used to seal or reinforce wounds that have been sutured or stapled; they can also be used with or without pressure over an injured area.

All available fibrin sealants are being produced by mixing fibrinogen with thrombin in different mediums, concentrations and additives such as Factor XIII. These techniques are prone to produce autoimmune reactions, in addition to severely limiting the activity and shelf life of components; fibrinogen is degraded by proteolysis and thrombin tends to cleave itself when is in solution. For this reason, fibrin components are often provided in lyophilized form, with freezing requirements and short shelf life. They must be used with sponges and/or films that are not convenient in trauma procedures.

In the process of developing a fibrin sealant for use in cases of non-compressible hemorrhage (ClotFoam application patent Ser. No. 12/419,734) it was determined that a fibrin monomer in acetic acid ready to polymerize at change of pH, offers substantial advantages for use in cases of non-compressible hemorrhage over cleavage of fibrinogen by thrombin, as generally used today. The advantages of incorporating a fibrin monomer in the sealant formulation are further described below.

Fibrin Sealants Current and Limitations.

Several products are commercially available (e.g., Tissel, Evicel, Gelfoam, Floseal, etc) [5-7], however, these products have significant limitations which have prevented their widespread use in trauma, emergency medicine and laparoscopic surgery; because current haemostatic agents require compression. In addition, all sealants expose thrombin to the immune system with the consequently risk of autoimmune disease, as well as other anaphylactic reactions due to plasma proteins. Furthermore the incorporation of fibrinogen and thrombin in solution exposes the sealant to a rapid proteolitic degradation and self cleavage.

Our Alternative Approach: Fibrin monomer produced by the methods described bellow is designed to be used as sealant component for that polymerizes from a fibrin monomer at a change of pH. The Monomer produced by this method is embedded in a scaffold and neutralized by components of this scaffold to achieve hemostasis.

The scaffold (e.g. CloFoam) presents to tissues fibrin monomer in acetic acid at a concentration of 12 mg/ml solution, which is embedded in an hydrogel that polymerizes by a change of pH, and that is rapidly stabilized by Factor XIII.[(8)]

The fibrin monomer delivered as a ready-to-polymerize fibrin in solution bypasses the fibrinogen cleavage process. When brought to neutral pH the polymerization of monomer and the following stabilization of the polymer is so rapid that the fibrin matrix forms in a matter of seconds, bonds with tissues in the midst of flowing blood, and remains at the lacerated site to form a clot. By including a fibrin monomer in acid solution rather than thrombin and fibrinogen, the sealant has a longer shelf life, better adhesion and avoids exposing thrombin to the immune system.

Advantages of Polymerization of Fibrin Monomer Over Fibrinogen Polymerization by Thrombin. Interactions Between Fibrin and Proteins Several hemostasis proteins, such as tissue-type plasminogen activator, plasminogen and FXIII, bind to fibrin. The fibrinous matrix of a wound also contains other plasma proteins, such as fibronectin and vitronectin. Fibronectin and vitronectin may act as a bridge molecule between smooth muscle cells and fibrin by binding to the a5 b1 or avb3 integrin receptor of cells. [9] In addition, fibronectin also binds fibrin exclusively through the aC-domain of the latter. This binding site is not accessible in fibrinogen, but becomes exposed in fibrin. Vitronectin directly associates with fibrin.

Thus, fibrin functions as bridging molecule for many types of cell-cell interactions and provides a critical provisional matrix at sites of injury. Fibrin-coated matrices have been reported to bind EC, smooth muscle cells, keratinocytes, fibroblasts, and leukocytes. These cells can bind directly to fibrin via cell surface integrin receptors and non-integrin (e.g. VE-Cadherin, ICAM-1, P-selectin, and GPIba) receptors. [10]. Integrins, transmembrane cell adhesion molecules that consist of an alpha and beta subunits, have been demonstrated to bind to fibrin, and are aMb2 on leukocytes, allbb3 on platelets and avb3, avb5 and a5 b1 on EC and fibroblasts.

Clot retraction by nucleated cells is very important for proper wound healing [11]. Binding of a5b1 integrin to fibrin in the clot promotes the retraction of the clot and changes the shape of the cell [12]. The contribution of the avb3 integrin to clot retraction during vascular healing has been demonstrated in many studies as well as the involvement of the allbb3 and aMb2 integrins [13]

Integrins facilitate the binding of EC to ECM proteins. The Aalpha chain of fibrinogen contains RGD sequences at positions 95-97 and 572-574, The Aalpha 572-574 RGD sequence binds the avb3 integrin in humans. The Aalpha572-574 RGD sequence is also required for the interaction of fibrinogen with a5b1 integrin [14], which plays an important role in cell adhesion. However, these observations may be influenced by the albumin molecule that is bound to the free sulfhydryl-group of the truncated Aalpha chain of fibrinogen Nieuwegein molecule, which may affect the fibrin structure, and endothelial invasion, and tube formation in the fibrin matrix.

Fibrin can also stabilize the expression of avb3-integrin on cultured human microvascular EC and therefore promote migration of these cells on provisional matrix proteins. ECs interact with fibrin via a number of receptors, such as Inter-Cellular Adhesion Molecule 1 (ICAM-1), VE-Cadherin, CD-44, and integrins. It has been observed that ICAM-1 binds the 117-133 sequence on the fibrinogen gamma chain. The beta15-42 sequence on fibrin plays an important role during the process of neovascularization [15]. It has been demonstrated that a fragment corresponding to the first four extracellular domains of VE-cadherin (cadherin 5) binds to this sequence. The fibrin(ogen) Aalpha572-574 RGD sequence that binds integrin avb3 and a5b1, plays a significant role during angiogenesis.

The power to stick to the lacerated tissue in a pool of blood also depends on the cellular and matrix interactions. The characteristics of the fibrin itself, such as the thickness of fibers, number of branch points, porosity, permeability and other polymerization characteristics define the interactions between specific binding sites on fibrin, pro-enzymes, clotting factors, enzyme inhibitors, and cell receptors [24]. The structure of the fibrin matrix affects its biological function. For example, more coarse matrices show a faster fibrinolysis and the pH of the fibrin matrix determines the in-growth of tubular structures. Opaque matrices at pH 7.0 consist of thick fibers and tube formation proceeds at a faster rate than in transparent matrices at pH 7.8 that consists of thinner fibers [20]. Several conditions may affect fibrin structure, such as the clotting rate (can be modulated by concentration of thrombin and salt content), but also by the presence of metal ions, proteins and enzymes, the rate of polymerization (determined by FXIII concentration and FXIII activation rate), and the rate of lateral polymerization (affected by fibrinopeptide B release and cross-linking sites on alpha and gamma chains). Chloride ions have been identified as modulators of fibrin polymerization, because these ions control fiber size by inhibiting the growth of thicker, stiffer, and straighter fibers. Cost-effective methods of producing fibrin monomer: The preparation, properties, polymerization, equilibria in the fibrinogen-fibrin conversion, solubility, activation and crosslinking of fibrin monomer has been studied by several authors since 1968 (16-23). An experimental method for producing fibrin monomer was first described and published by Belitser et al (1968, BBA) (24) This method limits the production of monomer to a few milligrams per day.

Although U.S. Pat. No. 5,750,657 to Edwardson et al. describes a method of preparing a fibrin sealant utilizing a fibrin monomer composition, the ClotFoam sealant composition and use to which the production method of fibrin monomer herewith described is entirely novel and allows to produce the monomer in a cost-effective manner.

SUMMARY OF THE INVENTION

The present invention lies within the domain of methods for the production of biological adhesives and fibrin sealants, which are biodegradable and nontoxic, intended for therapeutic use, for example, as an intracavitary hemostatic agent for non-compressible hemorrhage. Fibrin monomer when polymerized and stabilized can sustain hemostasis in trauma cases for several hours. This time is sufficient to permit safe evacuation to definitive care centers, and prevent re-bleeding in cases of soft-tissue surgery.

Fibrin monomer in acid solution is an excellent hemostatic component to be used with scaffolds in non-compressible or minimally invasive procedures such as laparoscopic surgery, and gynecology as well as in other compressible techniques used in general surgery.

In one aspect, the present invention relates to three different methods to produce a biocompatible fluid which can be embedded in an adhesive hydrogel foam,

| | |
|---|---|
| CHUNK Method | Chromatography column w/ fritted Disc, PTFE stopcock plug (FIG. 1) |
| Column Chromatography Method | ADJUSTA-CHROM, recycling column, jacketed column (FIG. 2) |
| Dialysis Method | Regenerated Cellulose Dialysis Tubing, T2 Membranes: 6000 to 8000 Dalton MWCO (FIG. 3) | sponge, patch or any other technique used to seal tissue.

In another aspect, the invention relates to a process for cost-effectively producing such a monomer.

In yet another aspect, the invention relates to a method for preserving the activity of the fibrin sealant and reduce the risk of immunological reactions.

BRIEF DESCRIPTION OF THE DRAWINGS

FIG. 2. Column Method: Preparation and isolation
FIG. 3. Dyalisis Method: Preparation and isolation
FIG. 4. Fibrin Monomer by SDS-PAGE And Western Blot showing dimmer formation by traditional methods and by dialysis. Lane 1: Ladder. Lane 2: Fibrinogen (ERL), Authentic Sample & Starting Material (2 mg/mL ic); Lane 3: Fibrin Monomer obtained by one of the methods , namely Dialysis Method. Lane 4: Fibrin Monomer, prepared by Medved's et al. Method.

DETAILED DESCRIPTION

The present methods are related to a composition that comprises a solubilized fibrin monomer at 10 to 15 mg/ml concentration in acid media. Such composition is the result of a process for a) producing a non-cross-linked fibrin polymer; b) preparing monomeric fibrin by dissolving the fibrin polymer in acid media; and c) concentrating the fibrin monomer solution to the desired concentration d) including the necessary components to ensure covalent bonding following a change of pH.

Because the present composition includes a form of fibrin monomer which is temporarily inhibited from polymerizing, e.g., by lowering the pH, it can be applied to a patient to form a sealant/fibrin polymer together with scaffolds, as well as sponges or patches, without the need of special preparation and dilutions in media; and can be stored as a solution with minimal proteolytic degradation. Because polymerization does not require exogenous thrombin, and because the thrombin molecule is partially removed (Chunk and column) or totally removed upon dialysis, it does not present a risk of autoimmune disease as a result of thrombin not being exposed to the immune system. Upon application, such fibrin monomer can be converted back to a polymeric form, e.g., by raising the pH back to neutral, so that a fibrin polymer sealant is formed and further ensure that the polymerization becomes irreversible.

In the original method published by Belitser et al (1968, BBA) (24) the buffer is squeezed out of fibrin polymer mechanically. Namely the clot in a glass tube is wrapped around the glass rod and is pressed against the tube wall until as much as possible polymerization buffer is squeezed out, then the remaining buffer is washed out by dipping the rod with fibrin polymer into 0.15 M NaCl, and finally the polymer is dissolved in acetic acid. In our dialysis method everything occurs in closed dialysis tubing in one step. Namely, acetic acid replaces polymerization buffer in the tube upon dialysis (by diffusion) and dissolves fibrin polymer in the tube.

Although the compositions of the present invention can be prepared by any known/convenient means, the methods herewith described can be employed to produce large amount of monomer in a cost effective manner. This is a principal difference between the methods bellow described and the original experimental method (mechanical removal of polymerization buffer with subsequent dissolving fibrin clot in acetic acid versus diffusion-driven replacement of polymerization buffer with acetic acid that dissolves fibrin clot.) The methods herewith described makes the process of preparation much easier and allows preparation of large amounts of fibrin monomer in a comparatively short period of time. Another aspect is that we use a partially permeable membrane (dialysis tubing) for the exchange of polymerization buffer with acetic acid. This means that one can use the membrane with selected pore size diameter (MW cut of, or MWCO) to remove thrombin, plasminogen, or both from fibrin monomer. This also means that one can use some commercial ultrafiltration devices for large scale preparation of fibrin monomer}.

Fibrinogen derived from human plasma is treated with recombinant human thrombin to form a fibrin polymer in calcium ion-free buffer solution, which will be further treated to form a fibrin monomer, as described by Beltser et al. Dissolving the polymer, in an acid, provides a fibrin monomer solution. The low pH inhibits the fibrin from polymerizing and thus the fibrin monomer is considered nondynamic. Typically, to use the fibrin monomer solution as one component of a fibrin sealant it is co-administered with a material to initiate the polymerization of the fibrin monomer. For example, a pH 3.5 fibrin monomer solution can be co-applied with an alkaline solution pH 8.3 buffer, to raise the pH of the fibrin monomer thereby creating an environment where the monomer will polymerize to form a fibrin polymer, which is the sealant. Factor XIII as well as other transglutaminase enzymes can be added to stabilize the polymer together with a source of calcium ions to activate Factor XIII.

Preferred compositions of the present invention comprise about 10-15 mg/ml of fibrin monomer in acetic acid solution with a pH 3.5. The present composition will be ready to polymerize by raising the pH to 7.3 in the presence of 100 u/ml of Factor XIII and 20 mM $CaCl_2$ (calcium ions). High clotability is ensured by the inclusion of sodium chloride.

The methods to produce the preferred compositions to be included as part of a fibrin sealant system contain other important factors such as harvesting, extraction, purification and concentration of the fibrin monomer. The three polymerization/solubilization preparation method described bellow are a simple way of obtaining a yield of fibrin monomer superior to 90% and relative low labor effort. Also, when the compositions of the present invention are co-applied to a surgical site with an agent to render the fibrin monomer polymerizable and a source of calcium ions, the resulting sealants have stability without the need for added antifibrinolytic stabilizers, i.e., aprotinin and/or without the need to remove plasminogen.

Using the process described below, compositions of the present invention can be prepared.

Fibrin Monomer Preparation (a) CHUNK METHOD: The polymerization reaction for the Chunk method was performed using 0.5 mg/ml of fibrinogen to 0.1 u/ml of thrombin. The process uses $Ca^{++}$ to produce a fibrin polymer in 20 mM HEPES (pH 7.3); 300 mM NaCl HBS. First, 100 mg of lyophilized Fibrinogen are dissolved in 200 mL HBS (dilution of approximately 0.5 mg/mL) and kept on ice. Second, 4 mL of 5 U/mL Thrombin solutions in HBS buffer are freshly prepared and keep on ice. Third, the two solutions are mixed in 50:1, Fibrinogen to Thrombin ratio, and gently mixed to make homogeneous solution, which is incubated at 37° C. using either water bath or incubator for 2 hr.

Figure 1:
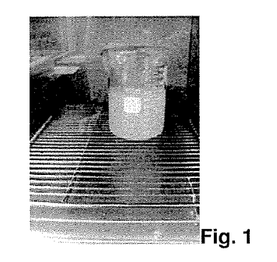
FIG. 1 Chunk method: (a) preparation; and (b) isolation.

After 1 hr in the incubator, the opaque/white gel mass is broken into pieces and then the suspension is transferred into a Kontes column w/fritted disc and Teflon stopcock[@]. With mild vacuum, the buffer is gently sucked out followed by 4x volumes of 150 mM NaCl buffer washing to remove all reaction buffers. Before adding ice cold 0.125% acetic acid solution (pH 3.5), the remainder of NaCl buffer is sucked out with care so the gel does not dry. The whole column with chunk solution is then stored overnight at 4° C. cold cabinet. The clear solution is collected in a tube at the bottom after filtration through this fritted disc column. FIG. 1 shows the preparation and harvesting of monomer by the chunk method. The clear cold acidic solution (~pH 3.45) is concentrated to 10-12 mg/mL using AMICON Ultra (10,000 MWCO, Millipore) centrifugal filter devices at 3000 RPM in a refrigerated centrifuge at 4° C. The concentration of fibrin monomer was measured by spectrophotometer (1 mg/ml/m1 has OD280=1.506) and gave yield of 67%.

| CHUNK Method | Chromatography column w/ fritted Disc, PTFE stopcock plug | Kontes[@] | Cat#420550-0450 |
| --- | --- | --- | --- |

Figure 2:
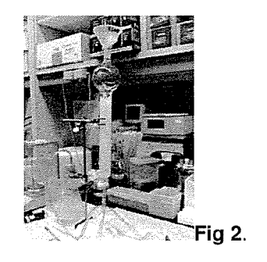

(b) COLUMN METHOD: The fibrin polymer to be harvested and dissolved by this method is prepared as described above in the chunk method by mixing 2 mg/ml of fibrinogen to 1.2 u/ml of Thrombin in 700 ml of HBS. The fibrinogen concentration in the column, 1-2 mg/ml, is higher than that in the chunk method. The reaction mixture is produced in an ACE GLASS jacked column[#]. The temperature of 37° C. is maintained by circulating warm water in the outer jacket. After two hours, the reaction buffer inside the column is exchanged with 2x volumes of 150 mM NaCl buffer using peristaltic pump at room temperature with outlet tube in a beaker which subsequently discarded. Next, 0.125% acetic acid solution (pH 3.5) is pumped through the column. When the pH of the fraction collected in the test tube changes to 3.5, the outlet tube is connected to inlet tube through the pump and the acidic solution is recirculated through the column overnight to dissolve the rest of the clot in the refrigerator at 4° C. FIG. 2 show the preparation and harvesting of monomer by the column method. The clear solution thus obtained after dialysis is then concentrated to a desired concentration by centrifugation using AMICON Ultra centrifugal devices as describe above. (~yield 76%)

| Column Chromatography Method | ADJUSTA-CHROM, recycling column, jacketed column | ACE GLASS[#] | Cat#5819 |
|---|---|---|---|

(c) DIALYSIS METHOD: The fibrin polymer to be harvested and dissolved by this method is prepared as described above in the column method by mixing 3 to 5 mg/ml of fibrinogen to 1.2 u/ml of Thrombin in 900 ml of HBS.

Figure 3:
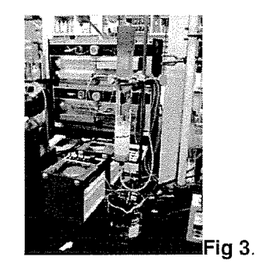

Thrombin is added into dialysis tube* 23 mm flat width× 100 mm long containing 3 to 5 mg/ml fibrinogen and HBS buffer, and sealed by clamps This mixture is at 37° C. for 1 hr. After the incubation, the tubes are rinsed with deionized water and dialyze directly against acetic acid solution, pH 3.45}. The tubes are rinsed with ice cold acetic acid solution (pH 3.5) followed by dipping into acetic acid solution with gentle stirring. After one hour period, the acetic acid solution is replaced by a fresh batch of acid and kept at 4° C. overnight with gentle stirring, to dissolve the clot inside the tubes. FIG. 3 shows the preparation and filtration of the monomer by the dialysis method. The clear solution thus obtained after dialysis is then concentrated to a desired concentration by centrifugation using AMICON Ultra centrifugal devices as describe above. (~yield >90%).

| Dialysis Method | Regenerated Cellulose Dialysis Tubing, T2 Membranes: 6000 to 8000 Dalton MWCO | Fisher Scientific* | Cat#21-152-3 |
|---|---|---|---|

EXAMPLES

Figure 4:
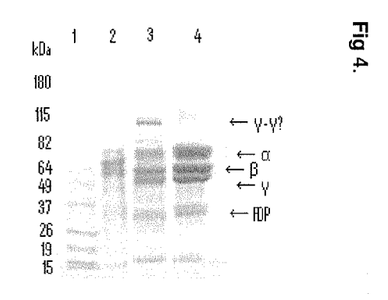
Figure 5:
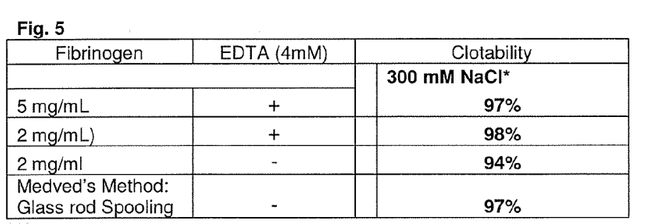
FIG. 5. Table iof fibrin monomer clottability as function of fibrinogen concentration and preservatives
FIG. 6. Western Blot of Polymerization and crosslinking of fibrin monomer compared to traditional cleavage of fibrinogen by thrombin. Lane 1: Ladder. Lane 2: Fibrin Monomer, CONTROL (final concentration 3.5 mg/ml). Lane 3: Fibrin Monomer neutralized w TBS (60 mM, pH 8.4) containing 2 mM CaCl2 and 0.1 U/ml initial concentration Thrombin. Lane 4: Fibrin Monomer neutralized w TBS (60 mM, pH 8.4) containing 2 mM CaCl2 and 0.01 U/ml initial concentration Thrombin in presence of 0.002 U/ml initial concentration Factor XIII Lane 5: Fibrinogen +Thrombin, Control.

1. Determination of Yields, Clotability and Formation of Covalent Bonds Following Polymerization
Determination of Fibrin Monomer Composition:

The fibrin monomer obtained by above methods were analyzed by SDS-PAGE and stained with Imperial Protein Stain (cat #24615, ThermoScientific) followed by Western Blot method. Immunoblots were developed by exposure to polyclonal sheep anti-Human Fibrinogen (Fg) affinity purified peroxidase conjugated antibody (Cat #: SAFG-APHRP, Enzyme Research Laboratory, IN) (1:40K) and compared with the authentic sample of Fibrin monomer obtained by the method of Medved et al (unpublished results?)[$] and also starting material Fibrinogen. The α, β, γ polypeptide chains of Fibrin monomer were at the same KDa level as the authentic sample and however at slightly lower KDa in comparison of Fibrinogen as expected. (FIG. 4)

Clottability

To 500 uL of 2 mg/ml Fibrin solution in AcOH (pH~3.4) with measured absorption at 280 nm , 500 uL of 1 M HEPES buffer with 4 mM CaCl2 was added immediately to bring pH ~7.2. The neutralizing buffer was 100 mM Tris (pH 7.5)+2 mM CaCl2+NaCl 1:1 Analyte (ACOH, pH 3.5): Neutralizing buffer. The final concentration of Analyte was 0.6 mg/mL. A 300 mM concentration of NaCl was to be used to get the right Ionic Strength. If very concentrated Analyte was used, 10-50×solution was used instead. The white clot was observed in less than 60 secs. After ½ hour, the suspension was centrifuged and the absorption of the supernatant was measured. The percentage of the ratio of the absorption of supernatant over the absorption of unreacted starting material is clotability of the substrate. The measured clotability was >94%.

Kinetics of Polymerization of the Fibrin Monomer

Figure 6:
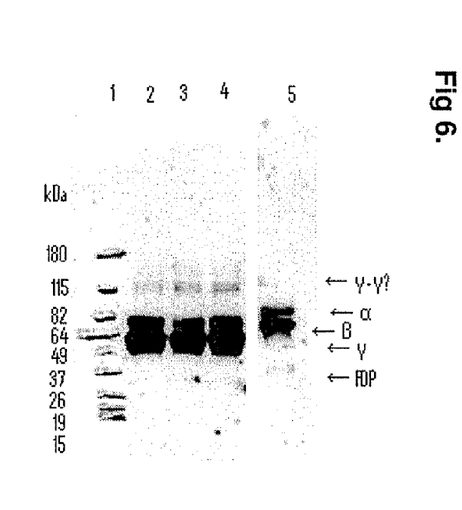

The polymerization of fibrin monomer was determined by detecting the formation of peptide chain fragments and its dimer such as D-dimer (γ-γ dimer) of fibrin(ogen) polymer formation was performed as follows. The sample from the above mixture was further dilution by 40% with Tris-HCl buffer (pH 7.2) before performing Western Blot. The samples were electrophoresed in 4-12% Tris-Glycine Gel (Cat #EC 6038, Invitrogen) and electrotransferred to a nitrocellulose membrane (Cat #LC2001, Invitrogen) by the procedure recommended in the protocol. The membrane was blocked with 5% milk powder in TBS for 1 hr and the chains of fibrin polymers were detected by the reaction with polyclonal sheep anti-Human Fibrinogen (Fg) affinity purified peroxidase conjugated antibody. (Cat #: SAFG-APHRP, Enzyme Research Laboratory, IN) (1:50K). Visualization of the peroxidase-labeled protein bands was performed by the procedure recommended by manufacturer using SuperSignal West Pico chemiluminescent substrate (ThermoScientific). FIG. 6

2. Shelf Life Experiments

Figure 7:
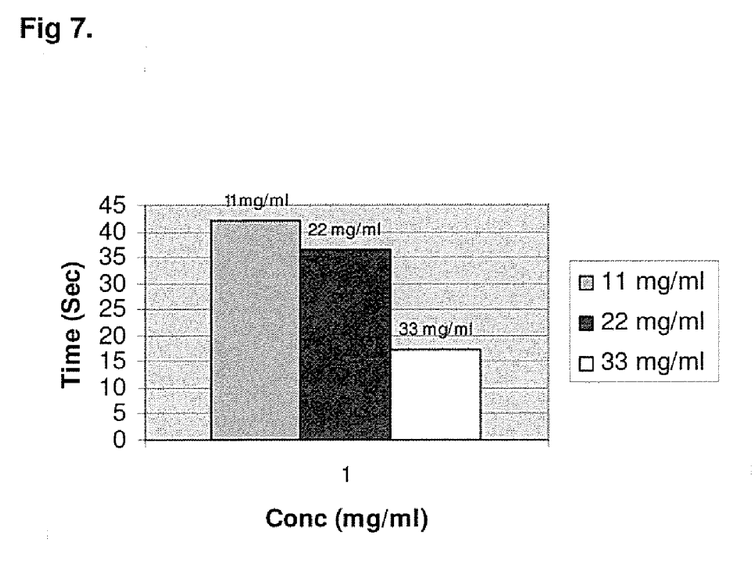
FIG. 7 Clotting time vs. Concentration of fibrin monomer in shelf-life studies for fibrin monomer in presence of Factor XIII (1.5 u/ml).

The purpose of these experiments was to establish that monomer does not degrade over time and under standard environmental conditions (4° C.). The shelf life of Fibrin monomer was analysed by SDS-PAGE and stained with Imperial Protein Stain (ThermoScientific). Fibrin monomers isolated by dialysis membrane method were studied in the presence (+/−) of 1% NaN3, as a preservative. The analyses of these samples were performed after 1, 4 and 15 days and compared with the Fibrin monomer samples obtained by independent method (Medved & Oglev, unpublished data) and stored for over 30 days at 4° C. FIG. 7.

Results: DSPage data show that the Fibrin Monomer produced by either method described in the this patent can be stored at 4° C. for over 30 days (lanes 3 and 9). However, after 4 days Fibrin Monomer even in presence of (+/−) 1% NaN3 (lanes 6 and 5, respectively) appears to degrade over 15 days (lanes 8 and 7, respectively) as evident by depletion of γ-chain.

Figure 8:
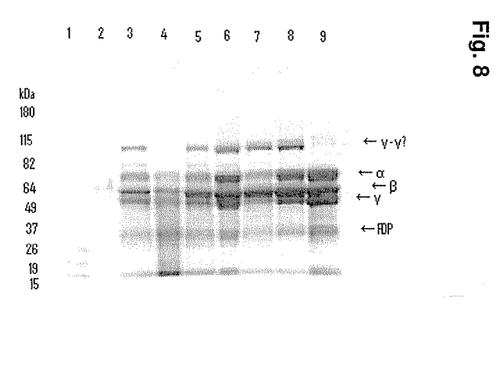
FIG. 8 Stability of Fibrin Monomer at different temperature conditions and storage and in presence of preservative (NaN$_3$). Lane 1: Ladder. Lane 2: Fibrinogen +Thrombin, CONTROL. Lane 3: Fibrin Monomer, prepared w/o EDTA, 4° C., 0 days. Lane 4: Fibrin Monomer, glass method, stored for >60 days at 4° C. Lane 5: Fibrin Monomer, 25° C., 4 days. Lane 6: Fibrin Monomer, 25° C., 4 days, w/NaN$_3$. Lane 7: Fibrin Monomer, 25° C., 15 days. Lane 8: Fibrin Monomer, 25° C., 15 days, w/NaN$_3$. Lane 9: Fibrin Monomer, glass method, stored for >30 days at 4° C.

Stability of Fibrin Monomer at different temperature conditions and storage and in presence of preservative ($NaN_3$)

Figure 9:
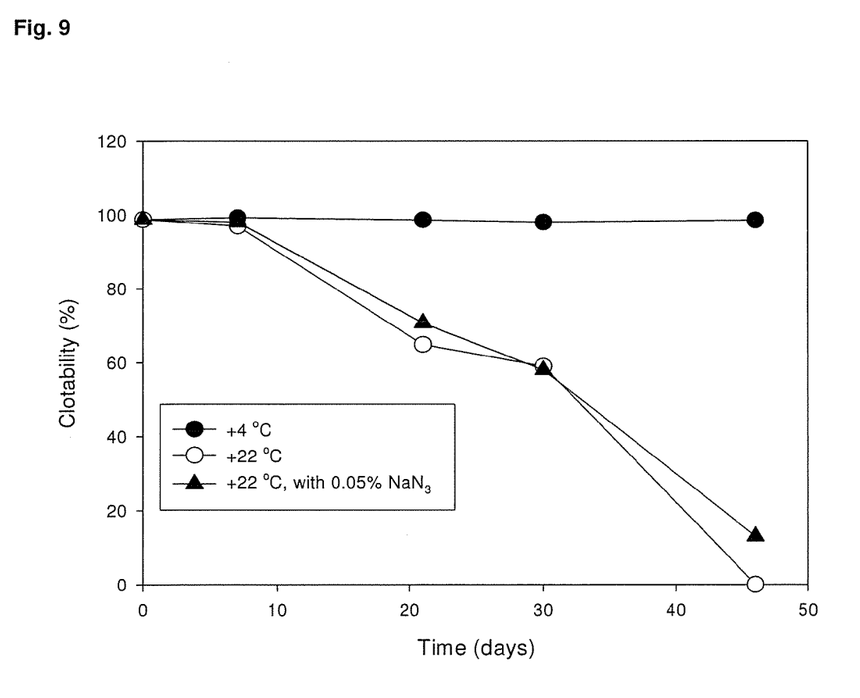
FIG. 9. Clottability graph as a function of temperature
FIG. 10. Western Blot-Degradation of fibrin monomer as a function of temperature.
Figure 10:
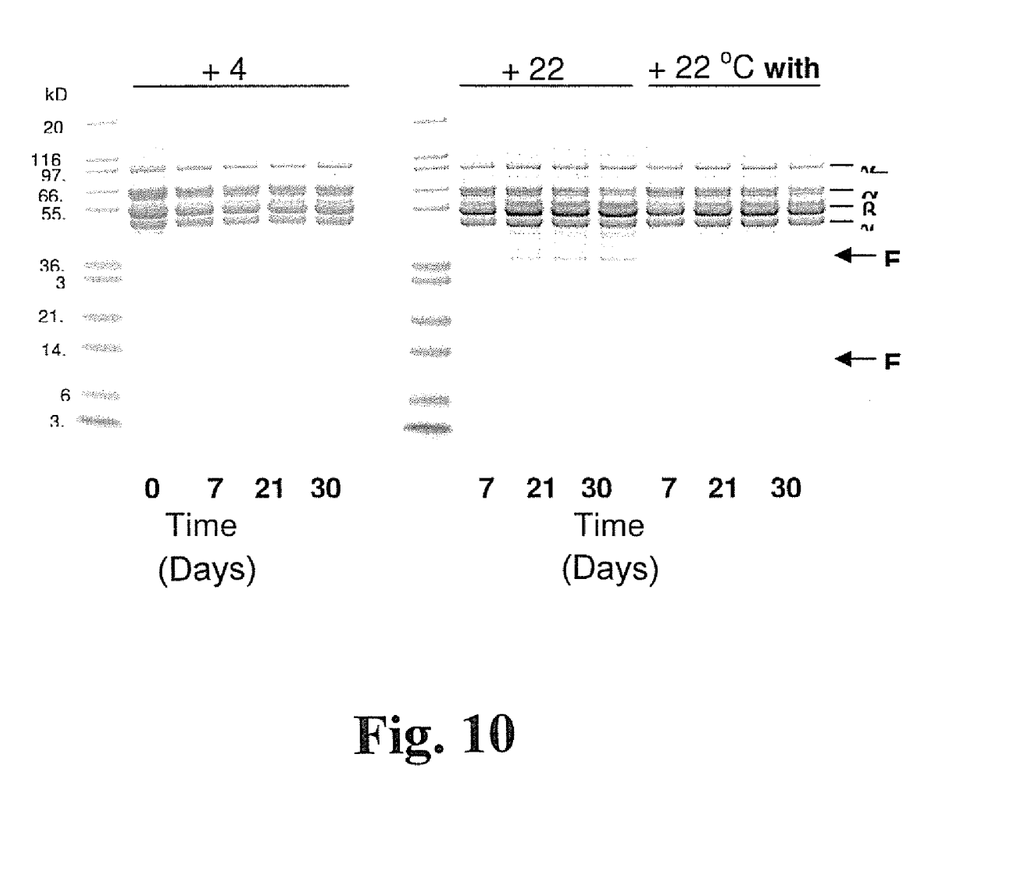

Ds-page assays indicate that monomer is stable at 4° C. for a minimum if 50 days and maintains its activity for 10 days at room temperature. FIGS. 8-10

3. Sterilization

These experiments are designed to establish that the Fibrin Monomer can be sterile filtered using 0.45 μm CA filter membrane and stored at 4° C. Method: 100 uL of sterile filtered Fibrin Monomer in AcOH (pH ~3.4) was uniformly spread over PDA (Cat# P2182, Sigma) and TSA (Cat #22091, Fluka) agar plates, respectively. After inoculation, the plates were incubated at 37° C. and observed daily for ten days. No statistically significant growth of any kind of microorganism was observed during this time period.

4. Testing the Sealing Efficacy of Fibrin Monomer in Animal Models

We have conducted the following studies in the swine model by embedding the fibrin monomer produced by each of the above methods in the ClotFoam scaffold. The Fibrin sealant consisted of a fibrin monomer mixed to a 2-part components of a gelatin hydrogel as described in provisional patents Studies were performed in liver grade III/IV wound open and close cavity model. Studies were conducted by University of Maryland Trauma Center and surgeons under the supervision of Grant Bochicchio, MD, FACS, at the Thomas Miller Animal facility in Baltimore.

Nine female Yorkshire crossbred swine, age 2.5 months, weighing 37±2 kg, were used. All animals were screened by a veterinarian to assure that they were in good health. Animals were allowed free access to water and to commercial laboratory swine food. Food was withheld the night before the study. All animals were maintained in an Association for Assessment and Accreditation of Laboratory Animal Care International-accredited facility, and all experimental manipulations were performed in accordance with the National Research Council's Guide for the Care and Use of Laboratory Animals. The protocol was approved by the Institutional Animal Care and Use Committee.

The swine were anesthetized with 1.5 ml buprenorphine and 0.3 ml glycopyrrolate intramuscularly. They were then intubated and placed on mechanical ventilation at a tidal volume 12 mL/kg, a rate of 10 respirations per minute, and 100% oxygen. Anesthesia was maintained using isoflurane.

Animals then underwent either grade 3 or 4 liver injuries via open laparotomy or by laparoscopy. For the purposes of this model, a grade 3 injury is defined as a 3 cm long full-thickness parenchymal laceration (created sharply by an 11 blade scalpel). After the liver was exposed, a spot in the middle of the liver was selected to produce the liver injury with a scalpel. The position was calculated by approximation to the suprahepatic vessels and some branches of the portal vein. The spot was marked with a marker. After the damage was induced, surgeons close the cavity, allowed for 30 seconds of massive bleeding before applying ClotFoam through a small perforation.

A grade 4 injury was a 10 cm deep parenchymal injury with a specially designed high-speed drill with a cutting drill bit creating an injury akin to a penetrating gunshot (GSW) wound (FIG. 1). Injuries were highly reproducible and severity was similar between the open and laparoscopic techniques. These injuries were consistent with the American Association for the Surgery of Trauma Organ Injury Scaling system.

Animals were randomized into 4 groups to date. Group 1 (n=2) consisted of animals who underwent grade 3 liver injuries through an open midline laparotomy and had open cavity ClotFoam application. In this group the agent was visually directed to the liver injury. Group 2 (n=2) consisted of animals who underwent grade 3 liver injuries through and open midline laparotomy and had closed cavity ClotFoam application. In this group the agent was administered into the peritoneal cavity blindly without direct injury visualization or direction. Group 3 (n=2) consisted of animals underwent grade 4 liver injuries through an open midline laparotomy without ClotFoam treatment (open controls). Group 4 (n=3) underwent grade 4 liver injuries through the laparoscopic technique without ClotFoam treatment (laparoscopic controls).

In all groups, 90 cc of ClotFoam was used for treatment. The ClotFoam was delivered via mixing syringes (FIG. 2) propelled into the abdominal cavity using pressurized carbon dioxide (approximately 50 psi). This created a homogenous hemostatic foam that actively clotted and sealed the injuries on both the visceral and diaphragmatic aspects of the liver.

Fluid resuscitation with Lactated Ringer's (LR) was begun immediately after injury. LR was infused as necessary to re-establish a MAP within at least 80% of the preinjury MAP if possible. Resuscitation was continued for the entire observation period. At the end of the 60 minute study, each animal's MAP and the total resuscitation volume infused were recorded.

After completion of the study period, the abdomen was examined. Liquid blood was suctioned. Blood clots were removed and weighed. In the gauze packing group, additional liquid blood loss was calculated by subtracting the wet gauze weight from dry gauze weight. Total blood loss was determined by adding liquid and clotted blood losses.

Animal survival was defined as the presence of a heart rate at the end of the study period. At 60 minutes, surviving animals were euthanized with 10 ml of Euthasol.

Results

Nine animals were used in the study to date. Four animals were grade 3 liver injuries (2 open cavity ClotFoam applications and 2 closed cavity applications). End points for animals in Groups 1 and 2 (Grade 3 injuries) are shown in Table 1. Trend of mean arterial pressures (MAPs) are seen in FIG. 1.

TABLE 1

Outcome measures for Grade 3 liver injuries treated with ClotFoam. Group 1 = open cavity, Group 2 = closed cavity. All values reported as mean ± SEM

| Group | Survival Time (min) | Total Blood Loss (ml) | Fluid Requirement (ml) |
|---|---|---|---|
| 1 (n = 2) | 60 ± 0 | 300 ± 283 | 1500 ± 283 |
| 2 (n = 2) | 60 ± 0 | 600 ± 212 | 2175 ± 742 |

Controls: Five animals underwent grade 4 liver injuries (3 laparoscopic and 2 open) to validate the laparoscopic model against the established open model. These animals were not treated with ClotFoam. Endpoints are seen in Table 2 and FIG. 2.

TABLE 2

Outcome measures for Grade 3 liver injuries treated with ClotFoam. Group 3 = open laparotomy, Group 2 = laparoscopic. All values reported as mean ± SEM

| Group | Survival Time (min) | Total Blood Loss (ml) | Fluid Requirement (ml) |
|---|---|---|---|
| 3 (n = 2) | 26 ± 3 | 1900 ± 424 | 3050 ± 70 |
| 4 (n = 3) | 22 ± 11 | 1700 ± 200 | 2467 ± 569 |

However it was established that although the animal survived 1 hour, the clot strength is not sufficiently strong to sustain hemostasis for a longer period. Optimization suffi

What is claimed is:

1. A method of producing a selected desAB fibrin monomer, or fibrin II monomer in acetic acid solution, for subsequent polymerization and application as a fibrin sealant for hemorrhage, the method comprising the steps of:
   i. forming a selected desAB fibrin polymer, or fibrin II polymer, in a selected buffer solution by treatment of fibrinogen with thrombin in a dialysis tube;
   ii. dissolving the formed desAB fibrin polymer, or fibrin II polymer via dialysis against the acetic acid solution containing 0.125% acetic acid at about 4° C. to 8° C. so as to produce a selected desAB fibrin monomer in said acetic acid solution, thereby at least partially removing thrombin and plasminogen from the solution comprising the fibrin monomer and the acetic acid solution; and iii. adjusting the amount of desAB fibrin monomer in the acetic acid solution of pH about 3.5 at about 4° C. to a concentration generally within a range of about 10 mg/ml to 15 mg/ml, wherein the produced desAB fibrin monomer in said acetic acid solution has clotability over approximately 95%.

2. The method set forth in claim 1, wherein the concentration of desAB fibrin monomer in acetic acid solution is about 12 mg/ml, and the pH of the solution is about 3.5, ready for said subsequent polymerization upon an abrupt increase in pH to about 7.0.

3. The method set forth in claim 2, wherein adjusting the amount of desAB fibrin monomer in the acetic acid solution further comprises the step of abruptly increasing the pH of the solution to neutral pH by mixing the acetic acid solution with a basic solution or basic buffer so as to polymerize the desAB fibrin monomer.

4. The method set forth in claim 3, wherein the desAB fibrin polymer is rapidly stabilized/crosslinked by the addition of a transglutaminase enzyme in the presence of approximately 20 mM of calcium ions.

5. The method set forth in claim 2, wherein the desAB fibrin monomer is embedded in a selected scaffold, foam, or patch for use as the fibrin sealant.

6. The method set forth in claim 2, wherein the composition comprising the fibrin monomer in acetic acid solution is cured such that it produces a functional clot within about 2 minutes of its application to injured tissue of a patient.

7. The method set forth in claim 2, where the desAB fibrin monomer is depleted of the plasminogen and at least partially depleted of the thrombin.

8. The method set forth in claim 2, wherein the desAB fibrin monomer is depleted substantially of the plasminogen and the thrombin.

9. The method set forth in claim 2, wherein the produced desAB fibrin monomer is preserved at a temperature of about 4° C. for over approximately 12 weeks without loss of activity.

10. The method set forth in claim 2, wherein the composition comprising the desAB fibrin monomer in the acetic acid solution is further sterilized by filtration.

* * * * *